United States Patent [19]

Smith

[11] Patent Number: 4,704,123
[45] Date of Patent: Nov. 3, 1987

[54] SOFT INTRAOCULAR LENS

[75] Inventor: Gregory M. Smith, Rowland Heights, Calif.

[73] Assignee: Iolab Corporation, Covina, Calif.

[21] Appl. No.: 881,163

[22] Filed: Jul. 2, 1986

[51] Int. Cl.$^4$ .............................................. A61F 2/16
[52] U.S. Cl. ......................................................... 623/6
[58] Field of Search ............................................ 623/6

[56] References Cited

U.S. PATENT DOCUMENTS

| | | | |
|---|---|---|---|
| 3,711,870 | 1/1973 | Deitrick | 623/6 |
| 4,110,848 | 9/1978 | Jensen | 623/6 |
| 4,257,130 | 3/1981 | Bayers | 623/6 |
| 4,573,998 | 3/1986 | Mazzocco | 623/6 |

FOREIGN PATENT DOCUMENTS

| | | | |
|---|---|---|---|
| 2556665 | 6/1977 | Fed. Rep. of Germany | 623/6 |
| 2725219 | 12/1978 | Fed. Rep. of Germany | 623/6 |

OTHER PUBLICATIONS

"Pathologic Findings of an Extended Silicone Intraocular Lens" by Donald A. Newman et al, Journal of Cataract Refrac. Surg., vol. 12, May 1986, pp. 292–297.
"Early Experience with Staar TM Silicone Elastic Lens Implants" by Gerald D. Faulkner, M.D., Journal of Cataract Surgery, vol. 12, Jan. 1986, pp. 36–39.
Poly–HEMA as a Material for Intraocular Lens Implanation: A Preliminary Report, R. B. S. Packard et al., British Journal of Ophthalmology, 1981 pp. 585–587.
Clinical Report on the Implantation of Transparent Silicon Jelly Artifical Lenses, Jhung–Hua Wenko Tsaonih, Jan. 1981, 17(1):17–30 and English Translations.
The New Soft Intraocular Lens Implant, Keiki R. Mehta et al., American Intraocular Implant Society Journal, Oct. 1978, pp. 200–205.
Silicone Intraocular Lenses in Rabbits, Albert D. Ruedemann, Jr., M.D. Tr. Am. Ophth. Soc. vol. LXXXV, 1977.

Primary Examiner—Ronald L. Frinks
Attorney, Agent, or Firm—Donal B. Tobin

[57] ABSTRACT

A soft intraocular lens suitable for placement in the anterior or posterior chamber and either in or out of the capsular bag. The lens has a fenestrated haptic defined by an arcuate member including a tissue contact portion, beam portions and support portions which acting together keep the lens in contact with the eye during distortion and tend to cause the lens to vault posteriorly when compressed.

7 Claims, 10 Drawing Figures

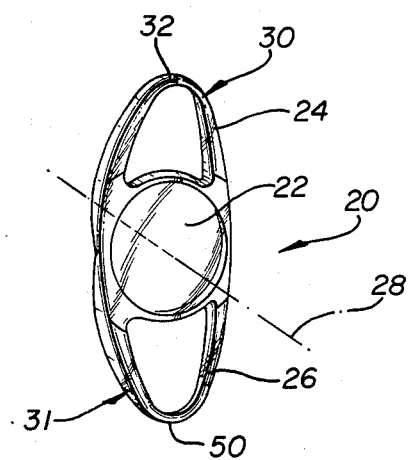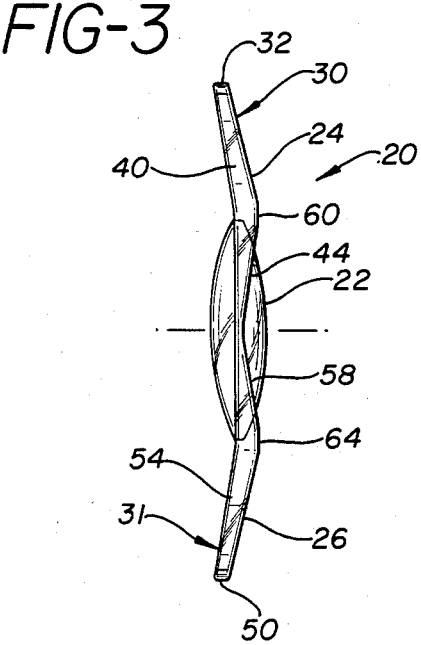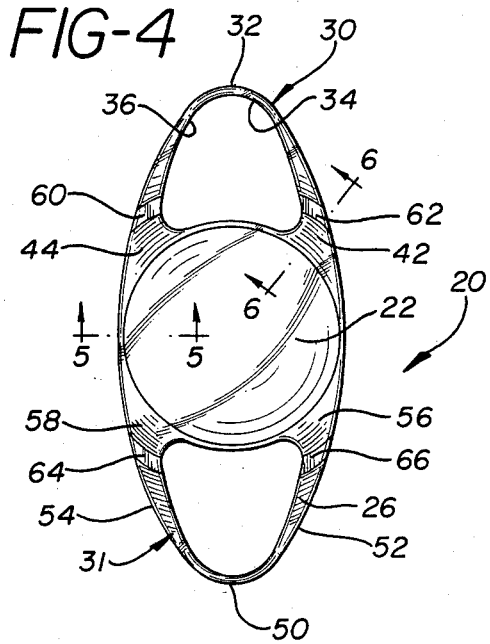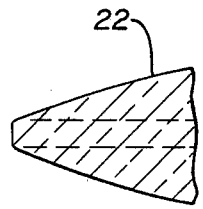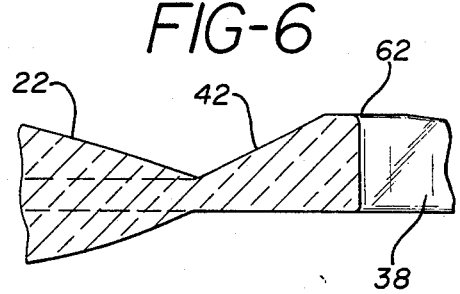

SOFT INTRAOCULAR LENS

FIELD OF THE INVENTION

The present invention relates to an intraocular lens and more particularly to an intraocular lens made of a soft material and having fenestrated haptics.

BACKGROUND OF THE INVENTION

It is now commonly accepted that the vision impairing disease known as cataracts can be alleviated by surgically replacing the natural lens of the eye with an artificial intraocular lens.

The anatomy of the eye is shown schematically in FIG. 7. The cornea 2 forms the front surface of the eye and connects with the ciliary muscle 3 from which iris 4 extends. Iris 4 divides the front portion of the eye into the anterior chamber 5 in front of iris 4 and the posterior chamber 6, behind iris 4. The pupil 7 is the aperture at the center of iris 4 through which light passes to posterior chamber 6 and onto the back of the eye (not shown).

The condition of cataracts is characterized by the clouding or opacification of the natural lens (not shown) of the eye which reduces the image forming capability or contrast sensitivity of the eye. The natural lens of the eye is encased in a capsular bag 8, as shown in FIG. 7, which is supported by suspensory ligaments, or zonules, 9 from ciliary muscle 3 near the base of iris 4, also called the ciliary sulcus.

During intraocular lens surgery, the natural lens of the eye is removed by a variety of methods well known to those skilled in the art. The front surface of the capsular bag is removed. The eye shown schematically in FIG. 7 has the natural lens and the front surface of capsular bag 8 removed so that the eye is ready for the insertion of the intraocular lens.

Still referring to FIG. 7, there is shown an incision 12 at the edge of the eye through which the lens will be inserted. The patient is usually lying on his back with the doctors standing facing the top of the patient's head. The incision would be made at a position called the superior part of the eye, and the intraocular lens is inserted from the superior portion of the eye toward the inferior portion of the eye. This terminology of inferior position and superior position is generally used in the field, and inferior positions are those spaced further away from the entrance incision, and superior positions are those spaced closed to the entrance incision.

An intraocular lens has two parts: a medial light focusing body called an optic and one or more haptics which extend from the optic to the surrounding anatomy of the eye. The haptic is meant to support the optic in the eye. The optic has an anterior surface facing forward toward the cornea and a posterior surface facing toward the retina. The optic has an optical axis which extends generally perpendicular to the plane of the optic.

Certain intraocular lenses of the kind shown in U.S. Pat. No. 4,573,998 to Thomas R. Mazzocco entitled "Method for Implantation of Deformable Intraocular Lenses" made of very soft flexible silicone type material. Although such lenses apparently make satisfactory intraocular lenses, there has been some concern expressed in the literature about the stability of fixation of such lenses to adjacent tissue. Questions have been asked whether a fibrous reaction that would enhance fixation occurs adjacent to silicone haptics, "Pathologic Findings of an Extended Silicone Intraocular Lens", Donald A. Newman et al., *Journal of the Cataract Refract. Surg.*, Vol. 12, May 1986. That paper also suggests that certain complications can be prevented by avoiding in-the-bag placement of the implant. The article continues, however, that the lens reported in the present study was not implanted in the capsular bag yet complications did occur. Other clinical investigators recommend not placing silicone implants in the bag. In "Early Experience with STARR TM Silicone Elastic Lens Implants" by Gerald D. Faulkner, M.D., *Journal of Cataract Refract. Surg.*, Vol. 12, January 1986, pp. 36–39, Dr. Faulkner comments that fibrous adhesions of the anterior capsular flap to the posterior capsule made the capsular bag space shorter than the implant, causing it to bend at the haptic-optic junction. The resulting tilt and decentration of the optic caused an increase in myopic astigmatism. Dr. Faulkner reports that Dr. Mazzocco and other doctors as well, reported the same complication in eyes in which the implant was placed in the capsular bag. Dr. Faulkner recommends that placing a silicone lens in the capsular bag should be avoided as it tends to result in decentration and tilting of the optic, which in most cases requires surgical intervention. Dr. Faulkner says that the flexibility of this elastic implant can be an advantage and disadvantage. It permits easier, less traumatic insertion through a smaller incision, but makes the implant vulnerable to forces caused by post-operative fibrosis that occur in some eyes. I believe it would be useful to have a soft intraocular lens which would be capable of placement in the bag or the ciliary sulcus and which would permit the fibrosis that occurs in some eyes to help hold the implant in place rather than to cause complications with the implant.

SUMMARY OF THE INVENTION

The present invention provides a soft one-piece intraocular lens with an optic and two fenestrated haptics extending from opposite peripheral edges of the optic. The lens may be used for anterior chamber placement or posterior chamber placement with the entire lens placed in the bag or with the lens haptics extending into contact with the ciliary sulcus. Previous lenses of this type like the lenses discussed in the Faulkner article are made of silicone and are so flexible that they require the extra rigidity provided by a solid flange-like haptics in order to permit them to keep their shape when implanted in the eye. The present fenestrated haptic has a specially constructed member extending about the periphery of the haptic and defining the fenestration. This member has three basic parts including a tissue contact portion remote from the optic, first and second beam portions extending from opposite ends of the tissue contact portion in a direction towards the optic and tapering so as to widen in a direciton measured in the plane of the fenestration when proceedings from the tissue contact portions toward the optic and also to widen in a direction measured generally parallel to the optic axis when proceeding from the tissue contact portion toward the optic. Each beam portion is connected to the optic by a support portion which widens in the plane of the fenestration as one proceeds from the beam portion toward the optic but narrows in the direction of the optical axis when one proceeds from the beam portion toward the optic. The tissue contact portion provides a very soft flexible area for contact with the anatomy of the eye. If the anatomy distorts so as to compress the lens, the tissue contact portion of the haptic easily deforms and spreads out to form a larger area of contact with the anatomy of the eye. The beam portions on the other hand tend to remain rigid. The tapering of the beam to widen as one moves from the tissue contact portion toward the optic tends to lend rigidity to the lens. The taper extends primarily posteriorly so that when the lens is compressed the optic will tend to vault posteriorly. The support portion tapers in the other direction so that its thickness measured in the direction generally parallel to the optic axis decreases as one proceeds from the beam toward the optic. This provides a support portion having a wide dimension in the plane of the fenestration of the haptic and a narrow dimension in a direction measured generally parallel to the optic axis to provide a point of preferential bending. If the haptic supports of this lens are compressed, the lens will tend to vault posteriorly and the beams will tend to remain rigid.

The fenestration allows fibrous growth to surround the tissue contact portion and hold the lens in place. For in-the-bag placement, part of the anterior flap of the capsule can close over the tissue contact portion to hold the lens in place. For sulcus placement, fibrous growth can capture the tissue contact portion to hold the lens in place.

These and other features and advantages of the present invention will become more apparent when taken in conjunction with the following detailed description of the preferred embodiments and the following drawings.

BRIEF DESCRIPTION OF THE DRAWINGS

FIG. 2 shows a front perspective of thelens shown in FIG. 1;

FIG. 3 shows side elevation of the lens of FIG. 1;

FIG. 4 shows a rear elevation of the lens of FIG. 1;

FIG. 5 shows a fragmentary sectional view taken along lines 5—5 in FIG. 4;

FIG. 6 shows a fragmentary view partly in section taken along lines 6—6 in FIG. 4;

DETAILED DESCRIPTION OF THE PREFERRED EMBODIMENT

Figure 1:
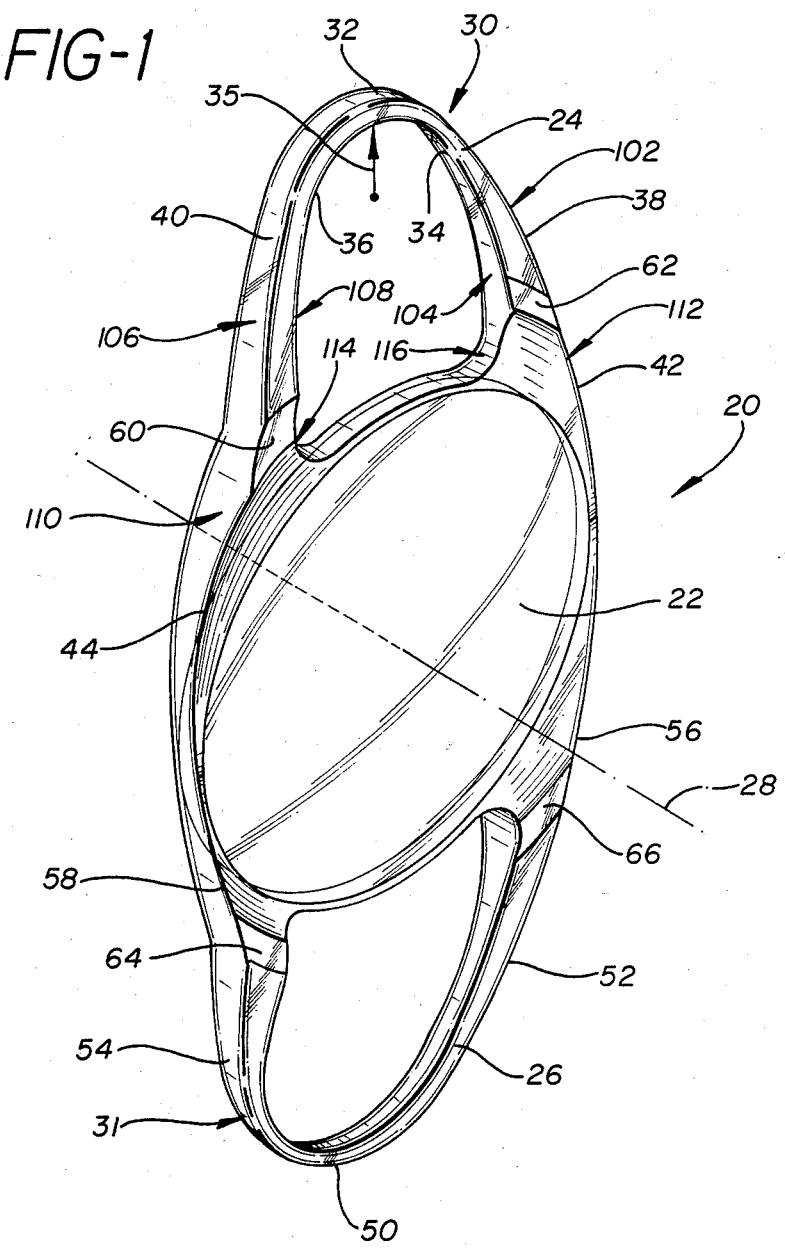
FIG. 1 shows an enlarged rear perspective view of the lens of the present invention emphasizing the details of the fenestrated haptic.

Referring now to FIG. 1, there is shown a perspective view of the rear of the intraocular lens 20 of the present invention having an optic 22 and support haptics 24 and 26. Optic 22 has an optical axis 28.

Haptics 24 and 26 extend from opposite peripheral portions of optic 22. Each of haptics 24 and 26 are fenestrated meaning that they are open. The fenestration of haptic 24 is defined by an arcuate member 30 which includes three basic segments. The first segment is a tissue contact portion 32 remote from optic 22 and having a first end and a second end roughly represented by reference characters 34 and 36 respectively. Since haptic member 30 is continuous member made of one piece of material, there is no discrete point which constitutes the first or second end of tissue contact portion 32. Tissue contact portion 32 blends smoothly with the remaining portions of haptic member 30 as will be discussed now. Tissue contact portion 32 has a first radius of curvature 35. Generally arcuate first and second beam portions 38 and 40 extend respectively from first end 34 and second end 36 of tissue contact portion 32 in a direction toward optic 22. Beam portion 38 is essentially the mirror image of beam portion 40. Arcuate beam portion 38 has an arcuate outer peripheral surface 102 and an arcuate inner peripheral surface 104. Arcuate beam portion 40 has an arcuate outer peripheral surface 106 and an arcuate inner peripheral surface 108.

Support portions 42 and 44 extend from spaced-apart peripheral portions of optic 22 and join beam portions 38 and 40 to optic 22. Support portion 44 has an arcuate outer surface 110 and support portion 42 has an arcuate outer surface 112. Support portion 42 has an arcuate inner surface 116 and support portion 44 has an arcuate inner surface 114.

Figure 8:
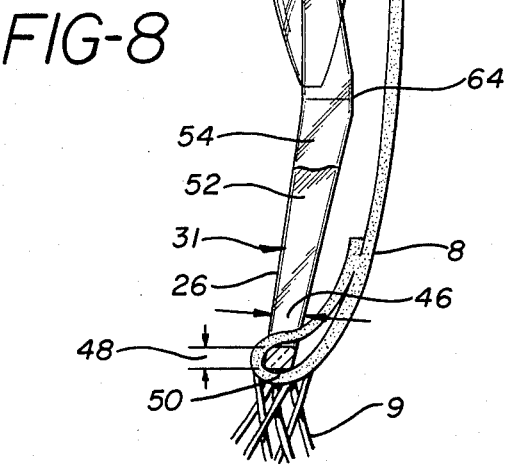
FIG. 8 shows a detailed view of the lens of the present invention in the capsular bag.

Referring now to FIG. 8, it can be seen that tissue contact portion 50 has a greater thickness 46 in a direction generally parallel to optical axis 28 than thickness 48 measured in a direction generally parallel to the plane of the fenestration.

Referring now to FIG. 4, it can be seen that the thickness of beam portions 38 and 40 measured in the plane of the fenestration increases when one moves from tissue contact portion 32 toward optic 22. It can be seen from FIG. 3 that the thickness of beam portions 38 and 40, measured in a direction generally parallel to optical axis 28 similarly increases as one proceeds from tissue contact portion 32 toward optic 22.

Referring to FIGS. 3, 4 and 6 and particularly FIG. 6, it can be seen that the thickness of support portion 42 measured in a direction generally parallel to optical axis 28 decreases as one proceeds from beam portion 38 toward optic 22. Referring to FIG. 4, it can be seen that the thickness of support portion 42 in the plane of the fenestration increases as one proceeds from beam portion 38 to optic 22.

Haptic 26 is essentially a mirror image of haptic 24 and has a corresponding arcuate member 31 including tissue contact portion 50, beam portions 52 and 54 and support portions 56 and 58.

Referring to FIGS. 3 and 4, it can be seen that haptic 24 has flat portions 60 and 62 on its posterior surface in the area between beam portion 40 and support portion 44 for flat portion 60 and beam portion 38 and support portion 42 for flat portion 62. Haptic 26 has similar flat portions 64 and 66.

Still referring to FIG. 3, it can be seen that haptics 24 and 26 bend anteriorly forming a small angle of between zero to fifteen degrees with the plane that is perpendicular to optical axis 28.

Figure 7:
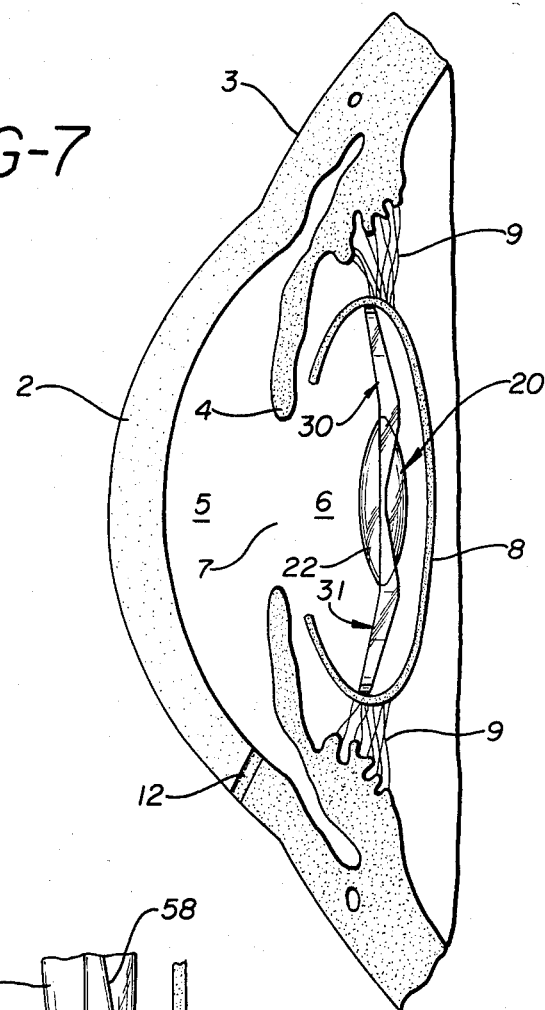
FIG. 7 shows a sectional view of the eye showing a lens of the present invention inserted in the capsular bag.

Referring now to FIG. 7, the lens 20 of the present invention is shown disposed in capsular bag 8 just after it has been inserted. FIG. 8 shows the lens 20 of the present invention with the anterior portion of the capsular bag 8 adhered through the fenestration onto itself to act as a means of anchoring lens 20.

It can be seen that the haptic members 30 and 31 are specially designed so that if they are compressed toward the optic by a distortion in the anatomy of the eye caused by rubbing, squinting or other motion, tissue contact portions 32 and 50 will spread into larger contact with the anatomy of the eye. The tapering of beam portions 38, 40, 52 and 54 have been designed to cause these beam portions to remain reasonably rigid under the influence of forces exerted by compressing the lens. The tapering of the support portion to become wider in the plane of the fenestration as one proceeds from the beam portions toward the optic and to become narrower in a direction measured substantially parallel to the optical axis tends to produce an area of preferential bending so that forces will concentrate at the narrow portions of the support portions causing the lens to tend to vault posteriorly when it is compressed in the plane generally perpendicular to the optical axis.

Figure 9:
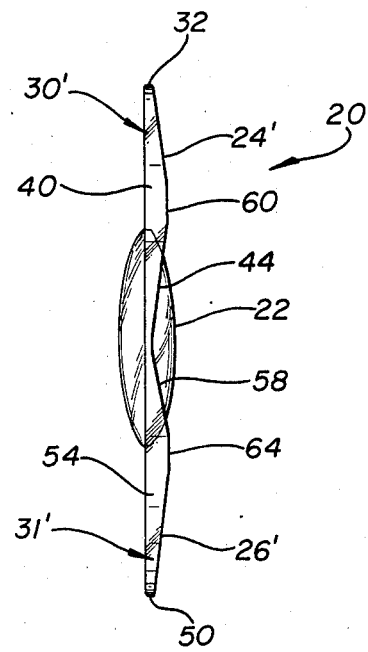
FIG. 9 shows a side elevation of a different embodiment of the lens of the present invention; and, FIG. 10 shows a sectional view of the eye with the lens of the present invention implanted in the ciliary sulcus.

Referring now to FIG. 9 there is shown another embodiment of the lens of the present invention. Lens 20' has similar haptics 24' and 26' which are substantially the same as haptics 24 and 26 of lens 20 shown in FIGS. 3 and 4 except that haptics 24' and 26' are aligned generally perpendicular to the plane of the optical axis rather than angled anteriorly.

Figure 10:
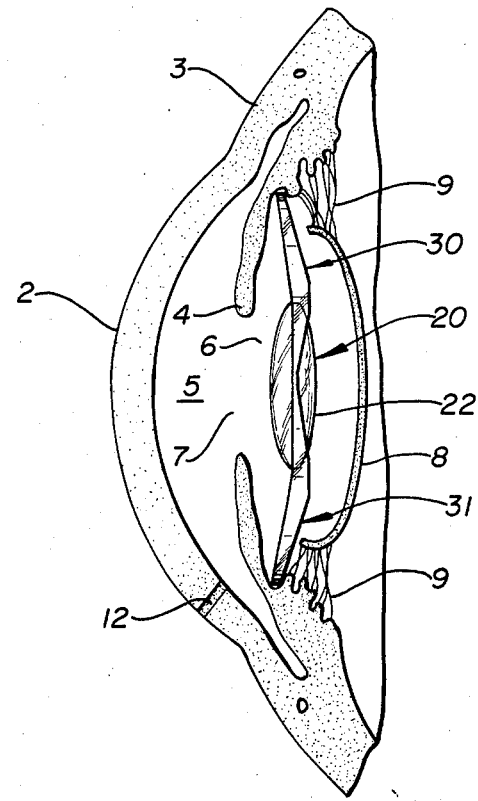

FIG. 10 shows the lens 20 of the present invention implanted in contact with the ciliary sulcus rather than in bag 8.

Thus, it can be appreciated that the lens of the present invention when subjected to compression in the plane perpendicular to the optical axis will tend to vault posteriorly as the haptic collapses rather than tilting or decentering. I have designed a lens which although made of a very soft silicone type material or comparable materials such as hydrogel, this lens is capable of accommodating the normal distortions of the eye without transmitting that distortion to the very flexible optic. I have designed a lens which is very soft and flexible. The normal distortions of the eye are absorbed in a specially designed fenestration haptic support so that the optic may be left in its proper position within the eye and with only minimal distortions of the optic.

The present invention has been described in conjunction with preferred embodiments. Those skilled in the art will appreciate that many modifications and changes may be made to the preferred embodiments without departing from the present invention. It is therefore, not intended to limit the present invention except as set forth in the appended claims.

I claim:

1. An intraocular lens comprising:
   an optic having a central light focusing portion and a surrounding peripheral portion said optic having an anterior surface, a posterior surface and an optical axis;
   first and second fenestrated haptic support members extending from opposite peripheral portions of said optic for supporting said optic in position within the eye;
   said fenestrations in each of said haptics defined by a member extending about the edge of said haptic said member having an arcuate outer peripheral surface and an arcuate inner peripheral surface and including:
      an arcuate tissue contact portion remote from said optic and having first and second ends said arcuate tissue contact portion having a first radius of curvature;
      a generally arcuate first beam portion extending from said first end of said tissue contact portion in a direction toward said optic;
      a first support portion having an arcuate outer surface connecting said first beam portion to said periphery of said optic;
      a generally arcuate second beam portion extending from said second end of said tissue contact portion toward said optic and substantially mirroring the arc of said first beam portion;
      a second support portion having an arcuate outer surface connecting said second beam portion to said periphery of said optic at a point spaced circumferentially apart from the point where said first support portion is attached to said periphery of said optic;
      the thickness of each of said first and second beam portions, measured in a direction generally parallel to said optical axis, increasing posteriorly as one moves from said tissue contact portion toward said optic;
      the width of each of said beam portions, measured in a direction generally parallel of the plane of the fenestration in said haptic also increasing as one moves in a direction from said tissue contact portion toward said optic; and
      the thickness of said tissue contact portion measured in a direction generally parallel to the optical axis being greater than the width of the tissue contact portion measured in a direction generally parallel to the plane of the fenestration in the haptic.

2. The intraocular lens of claim 1 wherein:
   the width of each of said support portions, measured in the plane of said fenestration, narrows as one proceeds from said peripheral edge of said optic toward said beam portion; and
   the thickness of each of said support portion, measured in a direction generally parallel to the optical axis, increases as one proceeds from said optic to said beam portion.

3. The intraocular lens of claim 1 wherein the curvature of said arcuate outer peripheral surface of each of said beam portions of said member is the same as the curvature of the arcuate outer peripheral surface of said support portions of said member.

4. The intraocular lens of claim 1 wherein the curvature of the arcuate inner peripheral surface of each of said beam portions of said member and the arcuate outer peripheral surface of each of said beam portions are the same but each emanates from a different center of curvature to provide the narrowing of the width of said beam portions, measured in the plane of the fenestration, as one proceeds in a directions away from the periphery of said optic toward said tissue contact portion.

5. An intraocular lens comprising:
   an optic having a central light focusing portion and a surrounding peripheral portion and an optical axis;
   first and second fenestrated haptic support members extending from opposite peripheral portions of said optic;
   each of said haptics having a generally arcuate outer perimeter including:
      an arcuate tissue contact portion remote from said optic and having first and second ends said arcuate tissue contact portion having a first radius of curvature;
      a generally arcuate first beam portion extending from said first end of said tissue contact portion in a direction toward said optic;

a first support portion having an arcuate outer surface connecting said first beam portion to said periphery of said optic;

a generally arcuate second beam portion extending from said second end of said tissue contact portion toward said optic and substantially mirroring the arc of said first beam portion;

a second support portion having an arcuate outer surface connecting said second beam portion to said periphery of said optic at a point spaced circumferentially apart from the point where said first support portion is attached to said periphery of said optic;

the curvature of said arcuate outer perimeter of said haptics on said support portions and said beam portions being the same;

the curvature of said arcuate outer perimeter of said haptics on said tissue contact portion being substantially less than the curvature of said beam portions;

each of said haptics having a generally arcuate inner perimeter defining said fenestration and including:

a compound curvature including a first radius of curvature of said tissue contact portion equal to the curvature of the outer perimeter of said haptic tissue contact portion and defining a constant thickness dimension across said tissue contact portion in a direction measured in the plane of said fenestration;

the curvature of said inner perimeter of said haptic beam portions being equal to one another and being substantially the same as the curvature of the outer perimeter of said haptic beam portions but aligned so that the dimension across the beam portion measured in the plane of the fenestration increases as one proceeds in a direction from the tissue contact portion towards the optic;

the curvature of said inner perimeter of said haptic support portions being equal to one another and being very much smaller than that of the radius of curvature of said tissue contact portion and smoothly blending between said beam portion and said optic.

6. The intraocular lens of claim 1 wherein said haptics both extend from said optic in the same plane, said plane being substantially perpendicular to the optical axis of said optic.

7. The intraocular lens of claim 1 wherein each of said haptics extends at an angle with respect to a plane perpendicular to the optical axis.

* * * * *